United States Patent [19]
Brinkmeyer et al.

[11] Patent Number: 5,671,153
[45] Date of Patent: Sep. 23, 1997

[54] CHEMICAL REACTOR FEED CONTROL

[75] Inventors: Francis M. Brinkmeyer; Steven D. Bridges; Ronald E. Miranda, all of Bartlesville, Okla.; Mike L. Facker, Sugar Land, Tex.

[73] Assignee: Phillips Petroleum Company, Bartlesville, Okla.

[21] Appl. No.: 393,768

[22] Filed: Feb. 24, 1995

[51] Int. Cl.⁶ .................. G06G 7/58; G06G 7/75
[52] U.S. Cl. .......... 364/502; 364/500; 364/173; 364/557; 364/510; 568/699; 422/110; 23/230
[58] Field of Search .................. 364/502, 500, 364/148, 166, 172, 509, 510; 568/668, 664, 669; 44/54, 53, 50; 222/1, 33, 36, 28; 422/110, 109, 111; 23/230

[56] References Cited

U.S. PATENT DOCUMENTS

| | | | |
|---|---|---|---|
| 3,135,807 | 6/1964 | Grasselli et al. | 260/614 |
| 4,290,110 | 9/1981 | Makovec | 364/500 |
| 4,332,590 | 6/1982 | Smith | 23/230 A |
| 4,482,969 | 11/1984 | Funk et al. | 364/500 |
| 4,979,091 | 12/1990 | Albers | 364/148 |
| 5,038,971 | 8/1991 | Gayer et al. | 222/1 |
| 5,428,577 | 6/1995 | Jerome | 430/30 |

*Primary Examiner*—Emanuel T. Voeltz
*Assistant Examiner*—Kamini Shah
*Attorney, Agent, or Firm*—George E. Bogatie

[57] ABSTRACT

In a process for manufacture of a chemical product in which a plurality of individual reactant containing feedstreams are combined to form a mixed feedstream for a reactor, and wherein at least one of the plurality of feedstreams is subject to variations in reactant concentration, and another one of the plurality of feedstreams is essentially stable in reactant concentration, a desired ratio of relative reactant concentrations in the mixed feedstream is maintained by a control system which infers a reactant concentration ratio in the mixed feedstream based on process measurements and feed parameters related to the plurality of feedstock containing streams prior to their being combined. In use, flow rate of the feedstream which is essentially stable in reactant concentration is manipulated to maintain the inferred reactant concentrations in the mixed stream.

14 Claims, 2 Drawing Sheets

CHEMICAL REACTOR FEED CONTROL

This invention relates to process control and more particularly to controlling a ratio of at least two reactants flowing to a chemical reactor. In another aspect this invention relates to method and apparatus for feed control to a chemical reactor used in the production of ether.

BACKGROUND OF THE INVENTION

In many chemical processes close control of the ratio of reactants is necessary to ensure that the reaction favors formation of the desired product. For example, it is known that a tert-alkyl ether can be prepared by reacting a primary alcohol with an olefin having a double bond on a tertiary carbon atom, as methanol reacts with isobutylene or isoamylene to form respectively methyl tert-butyl ether (MTBE) or tert-amyl methyl ether (TAME). The use of excess of methanol, however, renders the purification of ethers very expensive because of the formation of azeotropes, with the resulting difficulties in distillation of reaction effluent. Many etherification processes utilize feedstreams which are produced by some previous process and are often delivered directly to the ether reactor from a process such as a cracker unit or a dehydrogenation unit in the same or a nearby plant. Under such conditions reactive olefin constituents in the olefin feedstream may be present in variable concentrations due to process variations associated with its production in the previous process. Regardless of such variations it is desired to maintain a close ratio of olefin and alcohol reactants flowing to the ether reactor. Control in such a manner is both more in need and more difficult where the reactant is present in a feedstream in a relatively low concentration and/or subject to wide variations in concentration.

In an etherification process individual feedstreams of reactive olefin and alcohol are provided to a mixer with the mixed stream fed to the reactor. As used herein an individual stream is a stream containing at least one reactant but not all reactants required for a desired reaction. In the past typical control approaches for maintaining a constant concentration ratio of olefin to alcohol in the reactor feedstream relied on independently controlling the flow rate of the reactive olefin containing feedstream to a flow set point. Changes in concentration of reactive olefin in the olefin containing stream, which would cause a variation in the olefin to alcohol concentration ratio in the reactor feed, are detected by analyzing the mixed feedstream to determine the actual olefin/alcohol ratio, and then manipulating the individual alcohol stream to avoid a change in the ratio. While the above described control method which manipulates the flow of one or more individual feedstreams in response to measured analysis from a mixed feedstream has proven effective for controlling the olefin to alcohol concentration ratio, it is subject to certain limitations. For example, the analysis of a mixture containing alcohol and olefin components is complex and the analyzer is difficult to calibrate. Further the analysis equipment is difficult to maintain because of the alcohol present in the sample.

It is thus an object of this invention to reduce the cost for recovery of unreacted constituents in a reactor effluent stream.

Another object is to continuously control the flow of each reactive component in a mixed feedstream, with fixed ratios between reactive components, without measuring concentration of components in the mixed stream.

It is a more specific object of this invention to maintain a desired isoolefin to alcohol ratio in a feedstream to an ether reactor.

It is still another object is to improve efficiency in a process for producing a high purity ether product.

SUMMARY OF THE INVENTION

According to the present invention the foregoing and other objects are obtained by a method and apparatus for controlling reactor feed in which a plurality of individual feedstock containing streams, at least one of which is subject to variation of its desired reactant, are combined to form a mixed feedstream for the reactor. The desired ratio of reactive components in the mixed feedstream to the reactor is maintained by calculating the concentration ratio in the mixed feedstream to the reactor based on measured concentration and flow rates of the individual reactant feedstreams. Flow ratio control is then applied to the individual reactant streams to maintain the desired concentration ratio in the reactor feedstream.

In a preferred embodiment for a process including a hydrocarbon reactant containing feedstream having a variable concentration of its reactive component, and an alcohol reactant containing feedstream having a stable concentration of its reactive component, the hydrocarbon feedstream is analyzed to determine the concentration of the reactive component, and the flow rate of both the individual hydrocarbon and alcohol feedstreams are measured. Based on these measurements and the known stable concentration of the reactant in the alcohol feedstream, a concentration ratio of the reactive components for the mixed feedstream to the reactor is calculated. Flow ratio control is then applied to the individual reactant containing streams, where the output of a controller for the concentration ratio resets a flow ratio controller for the individual reactant feedstreams so as to maintain the desired reactant concentration ratio for the feedstream to the reactor.

Other objects and advantages of the invention will be apparent from the foregoing brief description of the invention and the claims as well as the detailed description of the drawings in which:

DESCRIPTION OF THE PREFERRED EMBODIMENT

Figure 1:
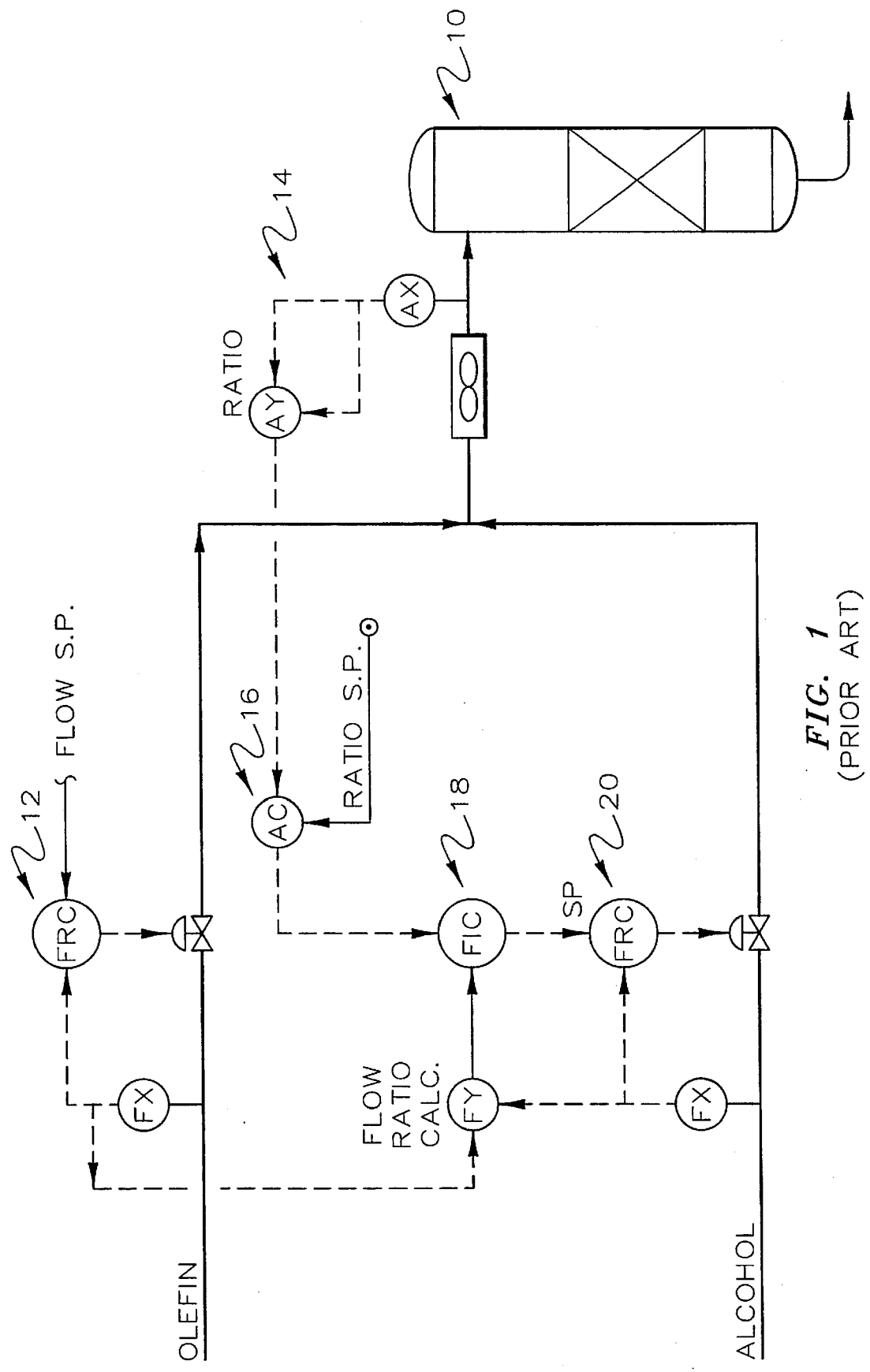
FIG. 1 is a prior art schematic illustrating blending control of two chemical components.

The invention is illustrated and described in terms of a process for the manufacture of methyl tert-butyl ether. The invention, however, is applicable to other manufacturing processes where it is desirable to control the ratio of reactants flowing to the reactor.

Essentially only two reactants, methanol and isobutylene are required to produced methyl tert-butyl ether. However, the blending control of this invention is applicable to the blending of more than two reactant streams.

Although the invention is illustrated and described in terms of a specific control system for feed control for the reactor, the invention is also applicable to different types and configurations of reactors which require blended feedstreams.

Dash lines, which designate signal lines in the drawings, are electrical or pneumatic in this preferred embodiment. However, the invention is also applicable to mechanical, hydraulic, or other signal means for transmitting information. In almost all control systems some combination of these types of signals will be used. However, the use of any other type of signal transmission, compatible with the process and equipment in use is within the scope of the invention.

The controller shown may use various modes of control such as proportional, proportional-integral, proportional-derivative, or proportional-integral-derivative. In this preferred embodiment, proportional-integral controllers are preferred but any controller capable of accepting two input signals and producing a scaled output signal, representative of the comparison of the two input signals, is within the scope of this invention. The operation of proportional-integral controllers is well known in the art. The output control signal of a proportional-integral controller may be represented as $$S = K_1 e + K_2 \int e \, dt$$

where:
S=output control signal
e=error between two input signals
$K_1$ and $K_2$=constants The scaling of an output signal by a controller is well known in control systems art. Essentially the output of a controller may be scaled to represent any desired factor or variable. An example of this is where a desired pressure and an actual pressure are compared in a controller. The output of the controller could be a signal representative of a desired change in the flow rate of some gas to make the desired and actual pressures equal. On the other hand, the same output signal could be scaled to represent a percentage or could be scaled to represent a temperature change required to make the desired and actual pressures equal. If the controller has an output that can range from 0–10 volts, which is typical, then the output signal could be scaled so that an output signal of 5 volts corresponds to 50 percent of some specified flow rate or some specified temperature.

The various transducing means used to measure parameters which characterize the process and the various signals generated thereby may take a variety of forms or formats. For example, the control elements of this system can be implemented using electrical analog, digital electronic, pneumatic, hydraulic, mechanical, or other similar types of equipment or combinations of one or more such equipment types.

The presently preferred embodiment of the invention utilizes distributed control in which the blending of feed components is managed by its own digital computer/controller, with the whole plant interconnected to form a single entity by a communication systems commonly known as data highways.

The distributed control system is used in the preferred embodiment of this invention to calculate the required control signals based on measured process variables and parameters as well as set points supplied to the control system. However, any computer control system having software that allows operation in a real time environment for reading values of external variables and transmitting signals is suitable for use in this invention.

Signal lines are also utilized to represent the results of calculations carried out in a digital computer and the term "signal" is utilized to refer to such results. Thus the term signal is used not only to refer to electrical currents or pneumatic pressures but it is also used to refer to binary representations of a calculated or measured value. The apparatus and method of the invention can accordingly be implemented using a wide variety of specific equipment available to and understood by those skilled in the process control art.

Referring now to FIG. 1 there is shown a conventional blending feed control for an ether reactor which is generally indicated at 10. Details of the process flow of material to the reactor will be more fully described in reference to FIG. 2 hereinafter. In this conventional control system of FIG. 1 an analyzer system generally indicated at 14, measures concentration of two reactants in the mixed feedstream and calculates a concentration ratio. The measured concentration ratio is compared to a ratio set point in the analyzer controller generally shown at 16, with the outputted analyzer control signal resetting a flow ratio controller which is generally shown at 18. The output of the flow ratio controller is used to reset a flow controller for the reactant stream having the most stable concentration to thereby maintain the desired analysis ratio shown at 16.

Figure 2:
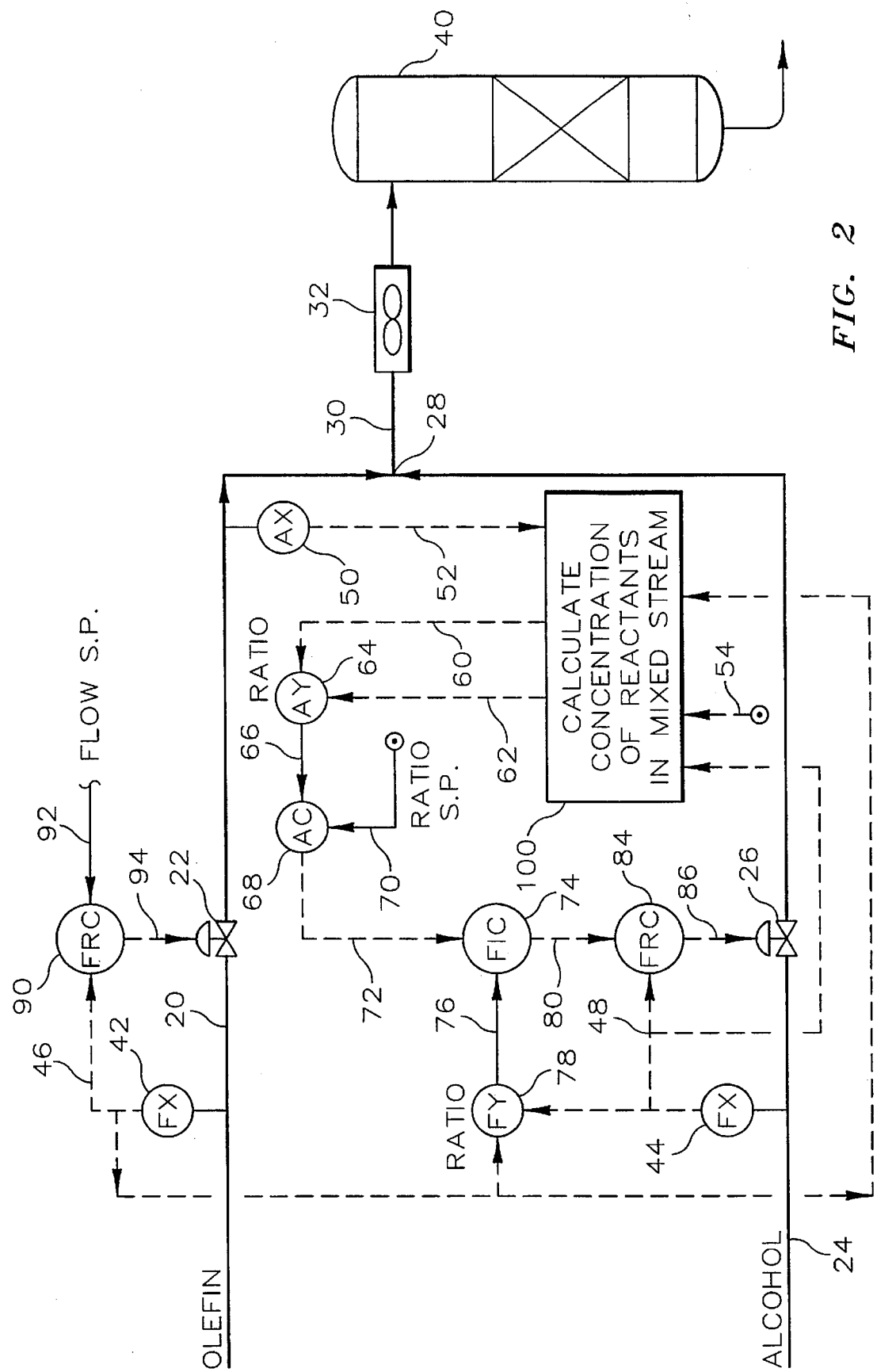
FIG. 2 is a schematic illustrating blending control of two reactive chemical components according to the invention.

Referring now to FIG. 2, there is illustrated the same process flow as shown in FIG. 1 but which is controlled according to this invention. A first conduit 20 having a flow control valve 22 associated therewith, and a second feed conduit 24 having a flow control valve 26 associated therewith are shown. The conduits 20 and 24 are adapted to provide flow of individual feedstock material through the associated valves 22 and 26 to a junction point 28 where they are combined to form a fresh feedstream flowing in conduit 30 to the reactor 40. A suitable means for mixing, such as a static mixer shown at 32, is provided to insure that the material flowing through conduit 30 is substantially homogenous before entering the reactor 40. In the preferred embodiment illustrated, the material carried in conduit 20 is a stream containing isobutylene such as e.g., a butane-butylene stream from a cracking unit which contains from about ten to about twenty five percent of the reactive isobutylene component. In such a stream, the isobutylene content is often relatively low and generally varies even from hour to hour. Alternately, the material carried in conduit 20 is a stream containing isobutylene from a dehydrogenation unit which contains up to about forty percent of the reactive isobutylene, but which isobutylene concentration may also vary. The feed material carried in conduit 24 is methanol, which is delivered from bulk storage and is therefore not subject to uncontrollable variations in overall composition or in methane content.

Operably associated with each conduits 20 and 24 is a respective flow transducer 42 and 44, each of which produces a respective flow signal 46 and 48 which is representative of the volume flow rate of feed material carried through the conduits with which it is associated.

Analysis transducer 50 is adapted to take a sample of fresh process feed material from the conduit 20 and to deliver, in response to the analysis of the reactant containing stream, an isobutylene concentration signal 52 which is representative of the volume fraction of isobutylene in the fresh feed flowing through conduit 20.

A computer calculation block 100, preferably associated with a distributed control system, receives as inputs thereto the flow rate signals 46 and 48, concentration signal 52 and an operator entered signal 54 which is representative of the stable methanol concentration of the material flowing in conduit 24. This methanol concentration signal would typically be set to about 100 percent. As previously noted, methanol is delivered from storage and is not subject to uncontrolled variation in overall composition or in methane content. In response to signals 46, 48, 52 and 54 computer calculation block 100 provides an output signal 60 representative of the concentration of isobutylene flowing in the mixed feedstream to the reactor, and another output signal 62 representative of the concentration of methanol flowing in the mixed feedstream to the reactor. Signal 60 and 62 are calculated in accordance with the following formulas:

$$C_{i,M} = (F_{t,O} \times C_{i,O})/(F_{t,O} + F_{t,A})$$
$$C_{m,M} = (F_{t,A} \times C_{m,A})/(F_{t,O} + F_{t,A})$$

where:
$C$ = Concentration, Vol. %
$F$ = Flow rate, bb/hr
Subscripts:
$t$ = all components    $o$ = olefin feedstream
$i$ = isobutylene    $A$ = alcohol feedstream
$m$ = methanol    $M$ = mixed stream The present invention encompasses a feed forward control scheme in which changes in reactant composition which would change the isobutylene to methanol ratio of the mixed feedstream are detected by measurements ahead of the mixing junction 28, and accordingly are made without waiting for a change to occur in the feedstream to the reactor. Corrections are made by calculating the isobutylene to methanol ratio in computation block 64, and providing signal 66 which inferentially represents the isobutylene to methanol ratio in the mixed feedstream to the reactor, as a process variable input to analyzer controller 68. Analyzer controller 68 is also provided with a set point signal input 70 which is representative of a desired isobutylene to methanol concentration ratio for the mixed feedstream.

In response to signal 66 and 70 analyzer controller 68 produces an output signal 72 which is responsive to the difference between signal 66 and 70. Signal 72 is scaled to be representative of the flow ratio of the materials flowing in the individual olefin feedstream 20 to the material flow in the individual alcohol stream 24. Signal 72 is provided as a variable input to flow controller 74. Also provided to a variable input of flow controller 74 is a flow ratio signal 76 which is representative of the flow ratio of material flowing in olefin stream 20 to the alcohol stream 24. Signal 76 is provided from the ratio computation block 78 based on flow signals 46 and 48.

Flow controller 74 provides an output signal 80 which is responsive to the difference between signal 72 and 76 and signal 80 is scaled to be representative of the actual flow rate of material in individual feedstream 24 required to make the flow ratio represented by signal 76 substantially equal to the flow ratio represented by signal 72. Signal 80 is provided a variable input to controller 84. Also provided to controller 84 is a signal 48 which is representative of the actual flow rate material in individual feedstream 24. Flow controller 84 provides an output signal 86 which is responsive to the difference between signals 80 and 48. Signal 86 is scaled to be representative of the position of control valve 26 required to maintain the flow ratio represented by signal 48 substantially equal to the flow rate represented by signal 80. The control scheme is completed with the addition of flow controller 90 which receives variable signal 46 representative of the actual flow rate in the olefin feedstream 20, and a set point signal 92 which is representative of a desired flow rate for feedstream 20. In response to signals 46 and 92 flow controller 90 provides an output signal 94 which is responsive to the difference between signals 46 and 92. Signal 94 is scaled to be representative of the position control valve 22 required to maintain the actual flow rate in feedstream 20 substantially equal to the desired flow rate represented by signal 92 and control valve 22 is manipulated in response to signal 94.

The invention had been described in terms of a presently preferred embodiment as illustrated in FIG. 2. Specific components which can be used in the practice of this invention as illustrated in FIG. 2, such as flow transducers and analyzer transducers, computer process control equipment are each well known, commercially available control components such as are described at length in Perry's Chemical Engineering Handbook, Sixth Edition, Chapter 22.

While the invention had been described in terms of the presently preferred embodiment, reasonable variations and modifications are possible by those skilled in the art within the scope of the described invention and the appended claims thereto.

That which is claimed:

1. Apparatus comprising:

a reactor;

a mixer for combining two fluid streams;

means for supplying a first feedstream containing a first reactant to an inlet of said mixer, wherein said first reactant is subject to variations in concentration in said first feedstream;

means for supplying a second feedstream containing a second reactant to said inlet of said mixer, wherein said second reactant is essentially stable in concentration in said second feedstream;

means for supplying a mixed feedstream from an outlet of said mixer to the feed inlet of said reactor;

means for establishing a first signal representative of the actual flow rate of said first feedstream;

means for establishing a second signal representative of the actual flow rate of said second feedstream;

means for establishing a third signal representative of the ratio of said first signal to said second signal;

means for establishing a fourth signal representative of the actual concentration of said first reactant in said first feedstream;

a computer programmed for calculating the concentration of said first reactant and said second reactant in said mixed feedstream based on said first signal, said second signal and said fourth signal, and wherein said computer establishes a fifth signal inferentially representative of the concentration of said first reactant in said mixed feedstream, and a sixth signal inferentially representative of the concentration of said second reactant in said mixed feedstream;

means for establishing a seventh signal inferentially representative of the ratio of said fifth signal to said sixth signal; and means for manipulating the flow rate of said second feedstream in response to said third signal and said seventh signal, to thereby maintain a desired concentration ratio of said first reactant to said second reactant in said mixed feedstream.

2. Apparatus in accordance with claim 1, additionally comprising:

means for establishing an eighth signal representative of said desired ratio of said first reactant and said second reactant in said mixed feedstream;

means for comparing said seventh signal and said eighth signal and establishing a ninth signal responsive to the difference between said seventh signal and said eighth signal, wherein said ninth signal is scaled to be representative of the flow ratio of said first feedstream to said second feedstream required to maintain the concentration ratio of said first reactant to said second reactant in said mixed feedstream represented by said seventh signal substantially equal to the desired ratio represented by said eighth signal.

3. Apparatus in accordance with claim 2, additionally comprising:

means for comparing said third signal and said ninth signal and establishing a tenth signal responsive to the difference between said third signal and said ninth signal, wherein said tenth signal is scaled to be representative of the flow rate of said second feedstream required to maintain the flow ratio represented by said third signal substantially equal to the ratio represented by said ninth signal.

4. Apparatus in accordance with claim 1, wherein said computer programmed for calculating the concentration of said first reactant and said second reactant in said mixed feedstream comprises computer means associated with a distributed control system.

5. Apparatus in accordance with claim 1, wherein said reactor comprises an ether reactor.

6. Apparatus in accordance with claim 1, wherein said first reactant is a hydrocarbon selected from the group consisting of isobutylene and isoamylene, and said second reactant is an alcohol selected from the group of alcohols consisting of methanol and ethanol.

7. Apparatus in accordance with claim 1, wherein the calculated concentration of said first and second reactants is additionally based on a constant number representative of the concentration of said second reactant in said second feedstream.

8. A method for controlling the concentration ratio of reactants in a feedstream to a reactor, wherein a plurality of feedstock containing streams are combined to form a mixed feedstream, and wherein a first feedstream containing a first reactant is subject to variations in its reactant concentration, and a second feedstream containing a second reactant is essentially stable in reactant concentration, said method comprising the steps of:

establishing a first signal representative of the actual flow rate of said first feedstream;

establishing a second signal representative of the actual flow rate of said second feedstream;

establishing a third signal representative of the ratio of said first signal and said second signal;

establishing a fourth signal representative of the actual concentration of said first reactant in said first feedstream;

using a computer for calculating the concentration of said first reactant and said second reactant in said mixed feedstream based on said first signal, said second signal and said fourth signal, wherein said computer establishes a fifth signal inferentially representative of the concentration of said first reactant in said mixed feedstream, and a sixth signal inferentially representative of the concentration of said second reactant in said mixed feedstream;

establishing a seventh signal inferentially representative of the ratio of said fifth signal and said sixth signal; and manipulating the flow rate of said second stream in response to said third signal and said seventh signal, to thereby maintain a desired ratio of said first reactant to said second reactant in said mixed stream.

9. A method in accordance with claim 8, additionally comprising:

establishing an eighth signal representative of said desired ratio of said first reactant to said second reactant in said mixed feedstream; and comparing said seventh signal and said eighth signal and establishing a ninth signal responsive to the difference between said seventh signal and said eighth signal, wherein said ninth signal is scaled to be representative of the flow ratio of said first feedstream to said second feedstream required to maintain the ratio of said first reactant to said second reactant in said mixed feedstream represented by said seventh signal substantially equal to the desired ratio represented by said eighth signal.

10. A method in accordance with claim 9, additionally comprising:

comparing said third signal and said ninth signal establishing a tenth signal responsive to the difference between said third signal and said ninth signal, wherein said tenth signal is scaled to be representative of the flow rate of said second feedstream required to maintain the flow ratio represented by said third signal substantially equal to the ratio represented by said ninth signal.

11. A method in accordance with claim 8, wherein said first reactant is a hydrocarbons elected from the group consisting of isobutylene and isoamylene, and said second reactant is an alcohol selected from the group of alcohols consisting of methanol and ethanol.

12. A method in accordance with claim 8, additionally comprising:

using a constant number representative of the concentration of said reactant in said second feedstream for calculating the concentration of said first and second reactants.

13. Apparatus in accordance with claim 1, wherein said computer is programmed to calculate the concentration of said first reactant and said second reactant in said mixed feedstream in accordance with the following formulas:

$$C_{i,M} = (F_{t,O} \times C_{i,O})/(F_{t,O} + F_{t,A})$$
$$C_{m,M} = (F_{t,A} \times C_{m,A})/(F_{t,O} + F_{t,A})$$

where:
$C$ = Concentration, Vol. %
$F$ = Flow rate, bb/hr
Subscripts:
$t$ = all components  $o$ = olefin feedstream
$i$ = isobutylene  $A$ = alcohol feedstream
$m$ = methanol  $M$ = mixed stream.

14. A method in accordance with claim 8, wherein said step of using a computer for calculating the concentration of said first reactant and said second reactant in said mixed feedstream, comprises calculating said first reactant and said second reactant in accordance with the following formulas:

$$C_{i,M} = (F_{t,O} \times C_{i,O})/(F_{t,O} + F_{t,A})$$
$$C_{m,M} = (F_{t,A} \times C_{m,A})/(F_{t,O} + F_{t,A})$$

where:
$C$ = Concentration, Vol. %
$F$ = Flow rate, bb/hr
Subscripts:
$t$ = all components  $o$ = olefin feedstream
$i$ = isobutylene  $A$ = alcohol feedstream
$m$ = methanol  $M$ = mixed stream.

\* \* \* \* \*